(12) United States Patent
Chou et al.

(10) Patent No.: US 6,313,294 B1
(45) Date of Patent: Nov. 6, 2001

(54) PROCESS FOR PREPARING AMIDES

(75) Inventors: Wen-Chih Chou; Chang-Wei Tan; Shyh-Fong Chen; Hao Ku, all of Taipei (TW)

(73) Assignee: Development Center for Biotechnology, Taipei (TW)

(*) Notice: Subject to any disclaimer, the term of this patent is extended or adjusted under 35 U.S.C. 154(b) by 0 days.

(21) Appl. No.: 09/111,452

(22) Filed: Jul. 8, 1998

(30) Foreign Application Priority Data

Feb. 4, 1998 (TW) ............................................. 87105024 A

(51) Int. Cl.[7] ...................... C07D 239/72; C07D 409/06; C07D 405/06; C07D 239/80; C07D 239/84
(52) U.S. Cl. .................... 544/292; 544/286; 544/291; 544/337; 544/374; 544/379; 544/386; 548/132; 549/366; 549/487; 564/134; 564/135; 564/136; 564/137
(58) Field of Search ...................... 564/134, 135, 564/136, 137; 544/286, 291, 337, 374, 379, 386, 292; 548/132; 549/366, 487

(56) References Cited

U.S. PATENT DOCUMENTS

| | | | |
|---|---|---|---|
| 3,935,213 | 1/1976 | Hess | 260/256.4 Q |
| 4,001,237 | 1/1977 | Partyka et al. | 260/256.4 B |
| 4,001,238 | 1/1977 | Partyka et al. | 260/256.4 B |
| 4,062,844 | 12/1977 | Hammen | 260/256.4 Q |
| 4,093,726 | 6/1978 | Winn et al. | 424/250 |
| 4,098,788 | 7/1978 | Crenshaw et al. | 544/293 |
| 4,126,894 | 11/1978 | Winn et al. | 260/256.4 Q |
| 4,138,561 | 2/1979 | Crenshaw et al. | 544/284 |
| 4,188,390 | 2/1980 | Campbell | 424/251 |
| 4,315,007 | 2/1982 | Manoury | 424/251 |
| 4,701,527 | * 10/1987 | Koermer et al. | 544/277 |

* cited by examiner

Primary Examiner—Peter O'Sullivan
(74) Attorney, Agent, or Firm—Fish & Richardson P.C.

(57) ABSTRACT

The present invention provides a process for preparing an amide, which comprises reacting an amine with an ester in a molten form in the absence of a solvent.

14 Claims, No Drawings

PROCESS FOR PREPARING AMIDES

The present invention relates to a process for preparing an amide.

BACKGROUND OF THE INVENTION

Many conventional synthetic pathways exist for preparing amide compounds. For instance, the reaction of an amine and an ester in a solvent, a well-known basic organic reaction, can be used to form an amide. In particular, it is known that the formation of an amide linkage by the reaction of a primary amine with an ester in a solvent under heating is possible. Moreover, the formation of an amide by reacting a secondary amine and an ester, can require not only a solvent, but also a catalyst, such as Lewis acid, strong base, or enzyme.

From conventional methods, the syntheses of amides, such as N-substituted carbonyl alkylenediamines, have several common features outlined below.

(1) Typically, the starting material is the corresponding organic acid. The organic acid is activated to an acid chloride or acid anhydride of higher activity, which is then reacted with a diamine to form the desired N-substituted carbonyl alkylenediamine.

(2) Since acid chlorides or acid anhydrides are highly reactive, the diamine used, typically, is treated with hydrogen chloride, hydrogen bromide, acetic acid, or tert-butoxycarbonyl to protect one of the amine groups. This step helps to reduce the formation of undesired diamides. The desired N-substituted carbonyl alkylenediamine can be obtained by a de-protection step.

(3) The conventional synthesis, typically, requires at least four reaction steps to form the N-substituted carbonyl alkylenediamine product. Furthermore, the synthetic process does not have a desirably high yield of the N-substituted carbonyl alkylenediamine product (only about 40% to 70%), and chemical wastes are generated, thus causing environmental problems.

SUMMARY OF THE INVENTION

The invention features a novel preparation of amide compounds.

The present invention advantageously solves the above-mentioned problems, e.g., multiple step/complex process, low yield, and chemical waste, by providing a process for preparing an amide through one simple step having a high yield of the desire amide product. The starting materials are an amine and an ester, which can be directly reacted in a molten form to produce an amide without the use of solvents and catalysts.

In addition, amide compounds play a very important role in organic chemistry and are used in the synthesis of many compounds. For instance, amide compounds can be used as intermediates or precursors to form a desirable chemical product. For example, an N-substituted carbonyl alkylenediamine can be used as the intermediate for synthesizing compounds used as an antihypertensive drugs, e.g., quinazoline derivatives.

In one aspect, the invention features a process for preparing an amide which includes contacting, in the absence of a solvent, an amine with an acyclic ester, where both the amine and the acyclic ester are in a molten form.

The amine can be a diamine having a secondary amino group. Alternatively, the amine can be an alkylenediamine.

An aspect of the above-described process includes a process for forming an N-substituted carbonyl alkylenediamine, wherein the amine is

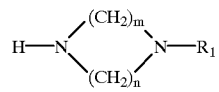

in which $R_1$ is selected from the group consisting of H, C1–8 alkyl, C1–8 alkenyl, C1–8 heteroalkyl, and C1–8 heteroalkenyl; m is 2 or 3; and n is 2 or 3; or

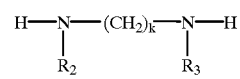

in which each of $R_2$ and $R_3$ is independently selected from the group consisting of H, C1–8 alkyl, C1–8 alkenyl, C1–8 heteroalkyl, and C1–8 heteroalkenyl; k is 1 to 8; and the ester is

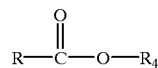

in which R is selected from the group consisting of C1–8 alkyl, C1–8 alkenyl, C3–8 cycloalkyl, C3–8 cycloalkenyl, C4–8 aryl, C2–8 heterocycle; and $R_4$ is C1–8 alkyl or C1–8 alkenyl.

A subset of the process for forming the above-described N-substituted carbonyl alkylenediamine features diamines having R1 selected from the group consisting of H, unsubstituted C1–8 alkyl, hydroxy substituted C1–8 alkyl, sulfhydryl substituted C1–8 alkyl, and amino substituted C1–8 alkyl.

A subset of the process for forming the above-described N-substituted carbonyl alkylenediamine features diamines having each of R2 and R3 independently selected from the group consisting of H, unsubstituted C1–8 alkyl, hydroxy substituted C1–8 alkyl, sulfhydryl substituted C1–8 alkyl, and sulfhydryl substituted C1–8 alkyl.

A subset of the process for forming the above-described N-substituted carbonyl alkylenediamine features esters having R selected from the group consisting of C2–8 heterocycle, unsubstituted C1–8 alkyl, hydroxy substituted C1–8 alkyl, and alkoxy substituted C1–8 alkyl.

Representative examples of R can include, for example,

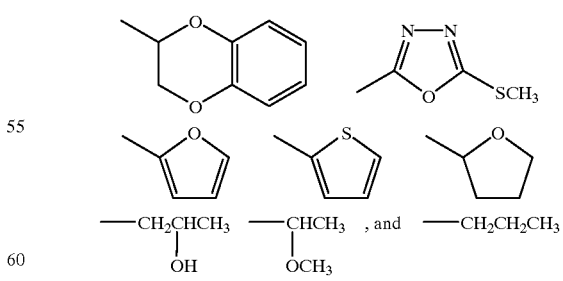

In yet, another subset of the above-described process, a quinazoline derivative is formed by contacting, in the absence of a solvent, an amine in a molten form with an ester in a molten form to form an N-substituted carbonyl alkylenediamine, wherein the amine is

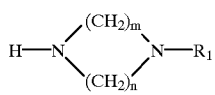

in which $R_1$ is selected from the group consisting of H, C1–8 alkyl, C1–8 alkenyl, C1–8 heteroalkyl, and C1–8 heteroalkenyl; m is 2 or 3; and n is 2 or 3; or

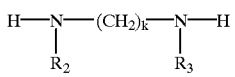

in which each of R2 and R3 is independently selected from the group consisting of H, C1–8 alkyl, C1–8 alkenyl, C1–8 heteroalkyl, and C1–8 heteroalkenyl; k is 1 to 8; and the ester is

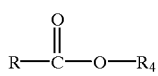

in which R is selected from the group consisting of C1–8 alkyl, C1–8 alkenyl, C3–8 cycloalkyl, C3–8 cycloalkenyl, C4–8 aryl, C2–8 heterocycle; and R4 is C1–8 alkyl or C1–8 alkenyl; and contacting said N-substituted carbonyl alkylenediamine with a quinazoline to form a quinazoline derivative, wherein said quinazoline derivative is

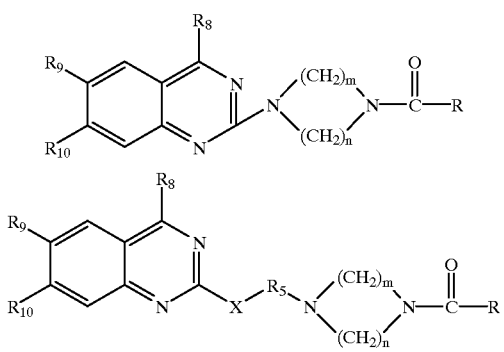

in which R, m, and n are defined above; and each of R8–R10 is independently selected from the group consisting of halogen, hydrogen, amino, C1–8 alkyl, C1–8 alkenyl, C3–8 cycloalkyl, C3–8 cycloalkenyl, C4–8 aryl, C1–8 alkoxyl, C1–8 alkylthio, C3–8 heterocycle; X is selected from N, O, or S; and R5 is selected from the group consisting of C1–8 alkyl, C1–8 alkenyl, C1–8 heteroalkyl, and C1–8 heteroalkenyl; or

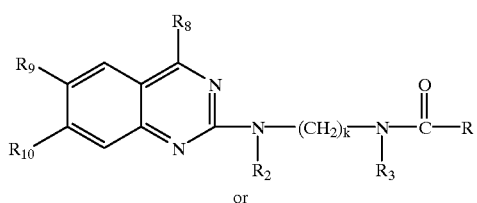

in which R, R2, R3, R8–R10, X, R5, and k are defined above.

A subset of the above-described process for forming the quinazoline derivatives features diamines having R1 selected from the group consisting of H, unsubstituted C1–8 alkyl, hydroxy substituted C1–8 alkyl, sulfhydryl substituted C1–8 alkyl, and amino substituted C1–8 alkyl.

A subset of the above-described process for forming the quinazoline derivatives features diamines having R5 selected from the group consisting of C1–8 alkyl, hydroxy substituted C1–8 alkyl, sulfhydryl substituted C1–8 alkyl, and amino substituted C1–8 alkyl.

A subset of the above-described process for forming the quinazoline derivatives features diamines having each of R2 and R3 independently selected from the group consisting of H, unsubstituted C1–8 alkyl, hydroxy substituted C1–8 alkyl, sulfhydryl substituted C1–8 alkyl, and amino substituted C1–8 alkyl.

In yet, another subset of the above-described process for forming the quinazoline derivatives features esters having R is selected from the group consisting of C2–8 heterocycle, unsubstituted C1–8 alkyl, hydroxy substituted C1–8 alkyl, and alkoxy substituted C1–8 alkyl. Representative examples of R can include, for example,

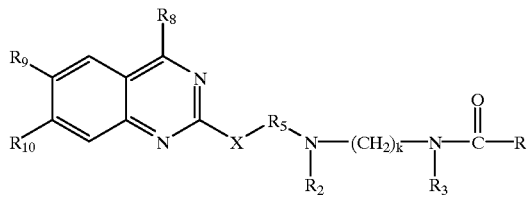

In another aspect, the invention features an N-substituted carbonyl alkylenediamine having the formula:

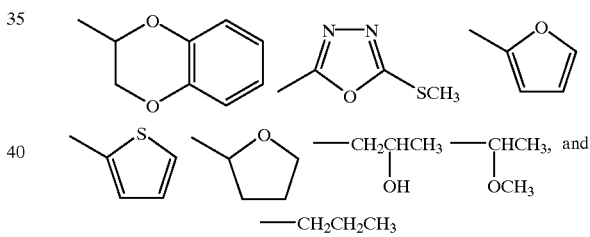

wherein n=2 or 3; m=2 or 3; and R1 is selected from the group consisting of C1–8 alkyl, C1–8 alkenyl, C1–8 heteroalkyl, and C1–8 heteroalkenyl; and R is selected from the group consisting of C1–8 alkyl, C1–8 alkenyl, C3–8 cycloalkyl, C3–8 cycloalkenyl, C4–8 aryl, and C2–8 heterocycle; or R1 is hydrogen and R is selected from the group consisting of C1–8 alkenyl, C3–8 cycloalkyl, C3–8 cycloalkenyl, C4–8 aryl, and thiophenyl.

A subset of the above-described N-substituted carbonyl alkylenediamines features compounds having R1 selected from the group consisting of H, unsubstituted C1–8 alkyl, hydroxy substituted C1–8 alkyl, sulfhydryl substituted C1–8 alkyl, and amino substituted C1–8 alkyl.

The N-substituted carbonyl alkylenediamine can be, for example, 1-(1,4-benzodioxan-2-yl-carbonyl)-4-(2-hydroxyethyl)-piperazine or 1-(thiophene-2-carbonyl)-piperazine.

In yet, another aspect, the invention features an N-substituted carbonyl alkylenediamine having the formula:

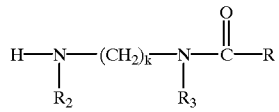

wherein each of R2 and R3 is independently selected from the group consisting of H, C1–8 alkyl, C1–8 alkenyl, C1–8 heteroalkyl, and C1–8 heteroalkenyl; k is 1 to 8; and R is selected from the group consisting of C1–8 alkyl, C1–8 alkenyl, C3–8 cycloalkenyl, C4–8 aryl, C2–8 heterocycle, the heteroatom being 1 to 4 of N, or 2 to 4 of O, S, or N, and thiophenyl.

A subset of the above-described N-substituted carbonyl alkylenediamines features compounds having each of R2 and R3 independently selected from the group consisting of H, unsubstituted C1–8 alkyl, hydroxy substituted C1–8 alkyl, sulfhydryl substituted C1–8 alkyl, and amino substituted C1–8 alkyl.

The N-substituted carbonyl alkylenediamine can be, for example, $N_1$-(1,4-benzodioxan-2-yl-carbonyl)-N2-methylpropylenediamine.

In another aspect, the invention features a quinazoline derivative having the formula:

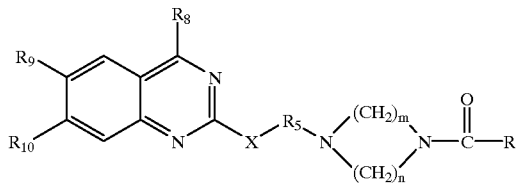

wherein each of R8–R10 is independently selected from the group consisting of halogen, hydrogen, hydroxy, sulfhydryl, amino, C1–8 alkyl, C1–8 alkenyl, C3–8 cycloalkyl, C3–8 cycloalkenyl, C4–8 aryl, C1–8 alkoxyl, C1–8 alkylthio, C3–8 heterocycloalkyl, and C4–8 heteroaryl; R is selected from the group consisting of C1–8 alkyl, C1–8 alkenyl, C3–8 cycloalkenyl, C3–8 cycloalkenyl, C4–8 aryl, C2–8 heterocycle; m is 2 to 3; n is 2 to 3; X is selected from N, O, or S; and R5 is selected from the group consisting of C1–8 alkyl, C1–8 alkenyl, C1–8 heteroalkyl, and C1–8 heteroalkenyl.

In yet, another aspect, the invention features a quinazoline derivative having the formula:

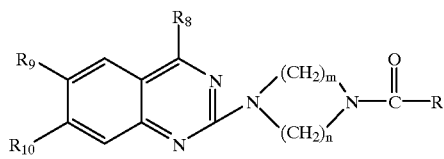

wherein each of R8–R10 is independently selected from the group consisting of halogen, hydrogen, hydroxy, sulfhydryl, amino, C1–8 alkyl, C1–8 alkenyl, C3–8 cycloalkyl, C3–8 cycloalkenyl, C4–8 aryl, C1–8 alkoxyl, C1–8 alkylthio, C3–8 heterocycloalkyl, and C4–8 heteroaryl; n=2 or 3; m=2 or 3; and R is selected from the group consisting of C1–8 alkyl, C1–8 alkenyl, C3–8 cycloalkyl, C3–8 cycloalkenyl, C4–8 aryl, and C2–8 heterocycle.

In still, another aspect, the invention features a quinazoline derivative having the formula:

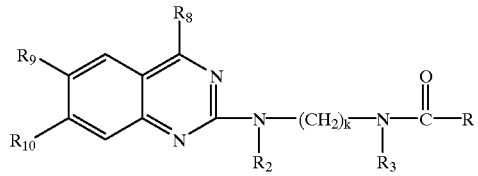

wherein R8–R10 are defined above; each of R2 and R3 is independently selected from the group consisting of H, C1–8 alkyl, C1–8 alkenyl, C1–8 heteroalkyl, and C1–8 heteroalkenyl; k is 1 to 8; and R is selected from the group consisting of C1–8 alkyl, C1–8 alkenyl, C3–8 cycloalkenyl, C4–8 aryl, C2–8 heterocycle, the heteroatom being 1 to 4 of N, or 2 to 4 of O, S, or N, and thiophenyl.

In still, another aspect, the invention features a quinazoline derivative having the formula:

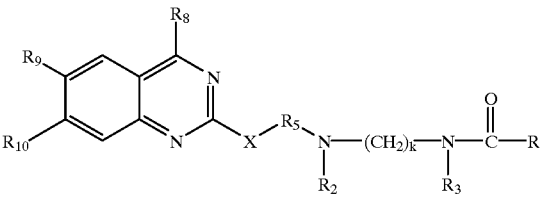

wherein each of R8–R10 is independently selected from the group consisting of halogen, hydrogen, hydroxy, sulfhydryl, amino, C1–8 alkyl, C1–8 alkenyl, C3–8 cycloalkyl, C3–8 cycloalkenyl, C4–8 aryl, C1–8 alkoxyl, C1–8 alkylthio, C3–8 heterocycloalkyl, and C4–8 heteroaryl; each of R2 and R3 is independently selected from the group consisting of H, C1–8 alkyl, C1–8 alkenyl, C1–8 heteroalkyl, and C1–8 heteroalkenyl; k is 1 to 8; R is selected from the group consisting of C1–8 alkyl, C1–8 alkenyl, C3–8 cycloalkenyl, C4–8 aryl, C2–8 heterocycle, the heteroatom being 1 to 4 of N, or 2 to 4 of O, S, or N, and thiophenyl; X is selected from N, O, or S; and R5 is selected from the group consisting of C1–8 alkyl, C1–8 alkenyl, C1–8 heteroalkyl, and C1–8 heteroalkenyl.

The term "heterocycle" refers to, for example, a cyclic substituent having 1 to 4 heteroatoms, e.g., O, N, or S. For example, the term "C2–8 heterocycle" refers to a cyclic substituent having 2–8 carbons and at least one heteroatom. Together, the carbon atoms and heteroatom(s) can form a single ring, fused ring, or bridged ring substituent. The "heterocycle" also can be aromatic. Examples of heterocycles include, but are not limited to pyridyl, furyl, pyrrolyl, thiophenyl, 1,4-benzodioxanyl, quinazolinyl. The term "C1–8 alkyl" refers to a linear or branched alkyl group containing 1–8 carbon atoms, including but not limited to methyl, ethyl, n-propyl, i-propyl, n-butyl, t-butyl, amyl, or amylmethyl. The term "C1–8 heteroalkyl" refers to a linear or branched alkyl group having 1 to 4 of O, N, or S atoms. The term "C1–8 alkenyl" refers to a linear or branched group containing 1–8 carbon atoms having at least two carbon atoms unsaturated to form a double bond. The double bond can be located anywhere along the C1–8 chain. The term "C1–8 heteroalkenyl" refers to a alkenyl group having 1 to 4 of O, N, S atoms. The term "sulfhydryl" refers to a —SH substituent.

The C1–8 alkyl, C1–8 alkenyl, C1–8 heteroalkyl, and C1–8 heteroalkenyl, C1–8 alkyl, C3–8 cycloalkyl, C3–8 cycloalkenyl, C4–8 aryl, C1–8 alkoxyl, C1–8 alkylthio, C2–8 heterocycle can be substituted with one or more substituent groups. Substituent groups, include, but are not limited to halogen, C1–3 alkyl, hydroxy, sulfhydryl, and aryl.

Unless otherwise defined, all technical and scientific terms used herein have the same meaning as commonly understood by one of ordinary skill in the art to which the invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the present invention will become apparent from the detailed description, and from the claims, given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

According to the present invention, an amine and an acyclic ester are reacted in a molten form in the absence of a solvent.

In order to synthesize the amide, the reactants (amine and ester) are heated to a molten state. The amine and ester can be subjected to heating, for example, heated to a temperature from 30° C. to 200° C. Preferably the temperature range is from about 100° C. to 120° C. In some instances, for example, the amine and ester are in a molten state at room temperature, e.g., liquids, and can be heated to a temperature from 30° C. to 200° C., preferably in the temperature range from about 100° C. to 120° C.

According to the present invention, the molar ratio of the amine to the ester can be 0.1 to 100. Preferably the molar ratio is about 1 to 3.

To make the reaction proceed more successfully and smoothly, a catalyst can be added, such as a Lewis acid, a strong base, or an enzyme. However, the catalyst is not necessary. For instance, a catalyst is not used in the examples described below and the yield of the amide is high.

The amine suitable for use in the present invention can be any amine that has nucleophilicity adequate to react with an ester. The amine can be a monoamine, a diamine, or a polyamine, which has primary amines or secondary amines. Preferably the amine includes at least one secondary amino group. The ester suitable for use in the present invention can be any acyclic ester.

The process of the present invention is particularly suitable for preparing an N-substituted carbonyl alkylenediamine. In such case, the amine suitable for use can be

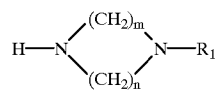

in which $R_1$ is selected from the group consisting of H, C1–8 alkyl, C1–8 alkenyl, C1–8 heteroalkyl, and C1–8 heteroalkenyl; m is 2 or 3; and n is 2 or 3.

Or, alternatively, the amine suitable for use can be

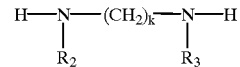

in which each of $R_2$ and $R_3$ is independently selected from the group consisting of H, C1–8 alkyl, C1–8 alkenyl, C1–8 heteroalkyl, and C1–8 heteroalkenyl; k is 1 to 8.

The ester suitable for use can be

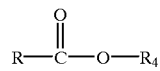

in which R is selected from the group consisting of C1–8 alkyl, C1–8 alkenyl, C3–8 cycloalkyl, C3–8 cycloalkenyl, C4–8 aryl, C2–8 heterocycle; and R4 is C1–8 alkyl or C1–8 alkenyl.

The resulting diamines, N-substituted carbonyl alkylenediamines, are

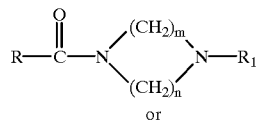

or

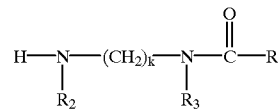

Representative examples of R1, R2, and R3 include, but are not limited to, H, unsubstituted C1–8 alkyl, hydroxy substituted C1–8 alkyl, sulfhydryl (—SH) substituted C1–8 alkyl, and amino substituted C1–8 alkyl.

Representative examples of R include, but are not limited to,

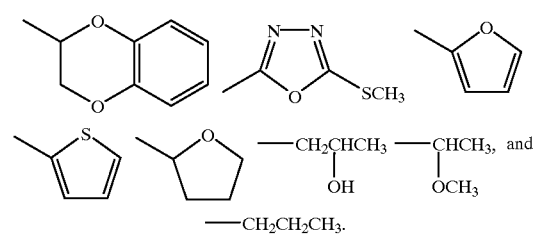

Examples of the N-substituted carbonyl alkylenediamines include, but are not limited to, 1-(1,4-benzodioxan-2-yl-carbonyl)-4-(2-hydroxyethyl)-piperazine, 1-(thiophene-2-carbonyl)-piperazine, and N1-(1,4-benzodioxan-2-yl-carbonyl)-N2-methylpropylene-diamine.

Amide compounds play a very important role in the synthesis of several compounds. For instance, they can be used as intermediates or precursors to form desired products. For example, the N-substituted carbonyl alkylenediamines, described above, can be used as intermediates or precursors for synthesizing compounds used as antihypertensive drugs.

The following examples are intended to more fully illustrate the process and the advantages of the present invention without limiting its scope, since numerous modifications and variations will be apparent to those skilled in the art.

EXAMPLES

Example 1

Preparation of 1,4-benzodioxan-2-ethylcarboxylate

Ortho-dihydroxybenzene (11 g, 100 mmol) and anhydrous acetone (70 mL) were refluxed under nitrogen. Potassium carbonate (5 g, 36 mmol), dibromoethyl propionate (6.56 g, 25.3 mmol) were added portion-wise in sequence over a period of 1.5 hours. After 4 hours, the reaction was completed, which was confirmed by thin film chromatography. The crude product was cooled to room temperature, concentrated under reduced pressure to remove acetone, added with $NaHCO_3$ solution, and extracted with ethyl acetate. The organic layer was dried with anhydrous sodium sulfate, and condensed to afford 18.51 g the product (89% yield).

The product was colorless liquid; 1H NMR($CDCl_3$) d 1.32 (t, J=2.1 Hz, 3H), 4.29 (q, J=2.1 Hz, 2H), 4.41 (d, J=3.9 Hz, 2H), 4.85 (t, J=3.9 Hz, 1H), 6.89~6.94 (m, 3H), 7.01~7.06 (m, 1H).

Example 2

A Comparison of Synthetic Methods

As an illustration of the improved synthesis, 1,4-benzodioxan-2-ethylcarboxylate and piperazine were reacted to form N-(1,4-benzodioxan-2-ylcarbonyl)piperazine. Since piperazine includes secondary amines, it is known that the amidization reaction can proceed only in the presence of a solvent and catalyst, e.g., a Lewis acid, strong base, or enzyme. Therefore, the solvent, e.g, THF, acetonitrile, benzene, toluene, or chlorine-containing solvent, was used to dissolve 1,4-benzodioxan-2-ethylcarboxylate and piperazine. The reactants were dissolved in anhydrous THF and potassium carbonate was added to catalyze the reaction. The mixture was stirred under nitrogen and heated to 110° C. After extraction and purification, it was found that the yield of 1-(1,4-benzodioxan-2-yl-carbonyl)piperazine (compound 1) was very low. The yield was less than 5%. Most of the product was 1,4-benzodioxan-2-carboxylic acid, which was obtained from hydrolysis of the reactant 1,4-benzodioxan-2-ethyl carboxylate.

In addition, the same starting materials described above were reacted in a molten form without using any solvent, such that, the hydrolysis of the reactants can be prevented, and the molten reactants can be completely mixed. The results of this reaction, see Example 3 for details, were very successful. The yield of compound 1 was greater than 90%.

Example 3

Preparation of 1-(1,4-benzodioxan-2-yl-carbonyl) piperazine (Compound 1)

1,4-benzodioxan-2-ethylcarboxylate, (31.2 g, 150 -mmol) and piperazine (15.5 g, 180 mmol) were stirred under nitrogen and heated to 110° C. After 5 hours, the reaction was completed, which was confirmed by thin film chromatography. The crude product was cooled to room temperature, extracted with chloroform, washed with $NaHCO_3$ solution and water. The organic layer was dried with anhydrous sodium sulfate, filtered to afford 34.96 g of compound 1 (94% yield).

The product, compound 1, is colorless solid; m.p. 84° C.–85° C.; 1H NMR($CDCl_3$) δ1.75 (brs, 1H, NH) 2.85~2.90 (m, 2H), 2.91~2.95 (m, 2H), 3.50~3.60 (m, 2H), 3.70~3.80 (m, 2H), 4.33 (dd, J=12.0, 8.1 Hz, 1H), 4.49 (dd, J=12.0, 2.5 Hz, 1H), 4.83 (dd, J=8.1, 2.5 Hz, 1H), 6.85~6.93 (m, 4H).

13C NMR ($CDCl_3$) d 43.18, 45.78, 46.93, 47.05, 65.22, 70.54, 117.28, 117.35, 121.49, 122.19, 142.55, 143.28, 164.84.

Example 4

Preparation of 1-(furan-2-carbonyl)-piperazine (Compound 2)

2-furan-methyl carboxylate (0.7 g, 5 mmol) and piperazine (1.3 g, 15 mmol) were stirred under nitrogen and heated to 110° C. After 3 hours, the reaction was completed, which was confirmed by thin film chromatography. The crude product was cooled to room temperature, dissolved with dichloromethane, extracted with 0.5 N hydrochloric acid solution (50 mL). The organic layer was washed with $NaHCO_3$ solution and water, dried with anhydrous sodium sulfate, filtered to afford a diamide compound (0.081 g). The water layer was adjusted to pH 10 by potassium carbonate solution and then extracted with chloroform. The extract was dried with anhydrous sodium sulfate and filtered to dry to afford 0.77 g of compound 2 (89% yield).

The product, compound 2, was a colorless solid; m.p. 68° C.–69° C.; 1H NMR($CDCl_3$) δ2.01 (s, 1H, NH), 2.87–2.92 (m, 4H), 3.70–3.81 (m, 4H), 6.45 (dd, J=3.5, 1.8 Hz, 1H), 6.95 (dd, J=3.5, 0.8 Hz, 1H), 7.45 (dd, J=1.8, 0.8 Hz, 1H).

The diamide compound was a white solid; m.p. 127° C.–128° C.; 1H NMR($CDCl_3$) δ3.90 (brs, 8H), 6.51 (dd, J=3.4, 1.8 Hz, 2H), 7.08 (d, J=3.5 Hz, 2H), 7.51 (d, J=1.8 Hz, 2H).

Example 5

Preparation of 1-(tetrahydrofuran-2 -carbonyl)-piperazine (Compound 3)

The procedures were the same as described in Example 3, except that tetrahydrofuran-2-methyl carboxylate (6.5 g, 50 mmol) was reacted with piperazine (5.16 g, 60 mmol) at 110° C. for 5 hours. After extraction and purification, 8.37 g of compound 3 was obtained (91% yield).

The product, compound 3, was colorless liquid; 1H NMR ($CDCl_3$) δ1.87–1.69 (m, 2H contain NH), 2.02–2.08 (m, 2H), 2.85–2.91 (m, 4H), 3.48–3.57 (m, 2H), 3.60–3.69 (m, 2H), 3.86–3.90 (m, 1H), 3.93–3.99 (m, 1H), 4.62 (dd, J=7.3, 5.4 Hz, 1H).

13C NMR ($CDCl_3$) δ25.58, 28.41, 42.97, 45.76, 46.24, 46.56, 68.93, 75.62, 169.79.

Example 6

Preparation of 1-(3-hydroxybutyryl)-piperazine (Compound 4)

The procedures were the same as described in Example 3, except that methyl-3-hydroxybutyrate (3.56 g, 27 mmol)

was reacted with piperazine (3.44 g, 40 moles) at 110° C. for 10 hours. After extraction and purification, 4.17 g of compound 4 was obtained (90% yield).

The product, compound 4, was pale yellow liquid; 1H NMR(CDCl3) δ1.34 (d, J=6.4 Hz, 3H), 2.42 (dd, J=16.4, 9.6 Hz, 1H), 2.59 (dd, J=16.4, 2.4 Hz, 1H), 2.75 (brs, 2H, NH and OH), 2.95–2.99 (m, 4H), 3.50–3.54 (m, 2H), 3.65–3.72 (m, 2H), 3.73–3.81 (m, 2H), 4.34 (ddq, J=9.6, 6.4, 2.4 Hz, 1H).

13C NMR (CDCl3) δ22.34, 40.82, 42.27, 45.57, 45.96, 46.34, 64.01, 170.76.

Example 7

Preparation of 1-(2-methoxypropionyl)-piperazine (Compound 5)

The procedures were the same as described in Example 3, except that methyl 2-methoxypropionate (1.18 g, 10 mmol) was reacted with piperazine (1.29 g, 15 mmol) at 110° C. for 6 hours. After extraction and purification, 1.54 g of compound 5 was obtained (90% yield).

The product, compound 5, was pale yellow semi-solid; 1H NMR(CDCl3) δ1.51 (d, J=6.8 Hz, 3H), 2.96–3.05 (m, 4H), 3.47 (s, 3H), 3.73–3.81 (m, 5H, contain NH), 4.27 (q, J=6.8 Hz, 1H).

13C NMR (CDCl3) δ17.51, 42.81, 45.76, 45.82, 46.12, 56.61, 76.81, 170.37.

Example 8

Preparation of 1-(butyryl)homopiperazine (Compound 6)

The procedures were the same as described in Example 3, except that ethyl butyrate (1.02 g, 10 mmol) was reacted with homopiperazine (1.50 g, 15 mmol) at 110° C. for 6 hours. After extraction and purification, 1.55 g of compound 6 was obtained (92% yield).

The product, compound 6, was pale yellow liquid; 1H NMR(CDCl3) δ0.99 (t, J=5.1 Hz, 3H), 1.66–1.73 (m, 2H), 1.78–1.86 (m, 2H), 1.93 (s, 1H, NH), 2.27–2.36 (m, 2H), 2.86–2.91 (m, 2H), 2.94–2.99 (m, 2h), 3.48–3.52 (m, 1H), 3.55–3.58 (m, 1H), 3.60–3.66 (m, 2H).

Example 9

Preparation of N1-methyl-N2-tetrahydrofuroylpropylenediamine (Compound 7)

The procedures were the same as described in Example 3, except that tetrahydrofuran-2-methyl carboxylate (1.3 g, 10 mmol) was reacted with N-methylpropylenediamine (1.76 g, 20 mmol) at 110° C. for 4 hours. After extraction and purification, 1.54 g of compound 7 was obtained (83% yield).

The product, compound 7, was pale yellow liquid; 1H NMR(CDCl3) δ1.63–1.68 (m, 2H), 1.73 (brs, 1H, NH), 1.81–1.89 (m, 2H), 1.98–2.05 (m, 1H), 2.17–2.26 (m, 1H), 2.39 (s, 3H), 2.57–2.64 (m, 2H), 3.26–3.34 (m, 2H), 3.80–3.85 (m, 1H), 3.86–3.91 (m, 1H), 4.30 (dd, J=8.4, 5.7 Hz, 1H), 7.22 (brs, 1H, NH).

13C NMR (CDCl3) δ25.37, 28.86, 30.16, 36.12, 37.26, 49.56, 69.20, 78.35, 173.23.

Example 10

Preparation of 1-(1,4-benzodioxan-2-yl-carbonyl)-4-(2-hydroxyethyl)-piperazine (Compound 8)

The procedures were the same as described in Example 3, except that compound 1S, 1,4-benzodioxan-2-ethylcarboxylate, (2.08 g, 10 mmol) was reacted with N-(2-hydroxyethyl)piperazine (1.56 g, 12 mmol) at 110° C. After extraction and purification, 2.91 g of compound 8 was obtained (98% yield).

The product, compound 8, was colorless solid; m.p. 61° C.–62° C.; 1H NMR(CDCl3) δ2.50–2.55 (m, 1H), 2.56–2.64 (m, 6H, contain NH), 3.60–3.65 (m, 2H), 3.66–3.70 (m, 2H), 3.79–3.85 (m, 2H), 4.33 (dd, J=11.9, 8.1 Hz, 1H), 4.49 (dd, J=11.9, 2.2 Hz, 1H), 4.84 (dd, J=8.1, 2.2 Hz, 1H), 6.85–6.93 (m, 4H).

13C NMR (CDCl3) d 42.04, 45.72, 52.47, 53.17, 57.90, 59.37, 65.16, 70.57, 117.26, 117.38, 121.52, 122.24, 142.48, 143.26, 164.82.

Example 11

Preparation of N1-(1,4-benzodioxan-2-yl-carbonyl)-N2-methylpropylenediamine (Compound 9)

The procedures were the same as described in Example 3, except that compound 1S, 1,4-benzodioxan-2-ethylcarboxylate, (2.08 g, 10 mmol) was reacted with N-methylpropylenediamine (0.89 g, 12 mmol) at 110° C. After extraction and purification, 2.4 g of compound 9 was obtained (99% yield).

The product, compound 9, was colorless solid; m.p. 60° C.–61° C.; 1H NMR(CDCl3) δ1.90 (brs, 1H, NH), 2.43 (s, 3H), 2.72–2.81 (m, 2H), 3.41–3.49 (m, 2H), 4.23 (dd, J=11.4, 7.2 Hz, 1H), 4.55 (dd, J=11.4, 2.7 Hz, 1H), 4.71 (dd, J=7.2, 2.7 Hz, 1H), 6.89–6.94 (m, 3H), 6.98–7.02 (m, 1H), 7.16 (brs, 1H).

13C NMR (CDCl3) δ35.86, 38.43, 50.32, 65.32, 73.23, 117.17, 117.48, 121.81, 122.23, 141.67, 143.23, 167.33.

Example 12

Preparation of 1-(thiophene-2-carbonyl)-piperazine (Compound 10)

The procedures were the same as described in Example 4, except that thiophene-2-methyl carboxylate 10S (1.56 g, 10 mmol) was reacted with piperazine (1.72 g, 20 mmol) at 110° C. After extraction and purification, 0.73 g of compound 10 (60% yield) and 0.1 g of a diamide compound 10' were obtained.

The product, compound 10, was pale yellow semi-solid; 1H NMR(CDCl3) δ1.98 (brs, 1H, NH), 2.86–2.91 (m, 4H), 3.67–3.72 (m, 4H), 7.02 (dd, J=5.1, 3.7 Hz, 1H), 7.25 (dd, J=3.7, 1.1 Hz, 1H), 7.42 (dd, J=5.1, 1.1 Hz, 1H).

The by-product 10' was white solid; m.p. 177° C.–180° C.; 1H NMR(CDCl3) δ3.84 (brs, 8H), 7.09 (dd, J=4.8, 3.8 Hz, 2H), 7.34 (d, J=3.8 Hz, 2H), 7.50 (d, J=4.8 Hz, 2H).

Example 13

Reaction Yields

The yields for compounds 1–10 described in Examples 3–12 are listed in the table below. In addition, the yield of compound 1 formed by reacting an amine and an ester in the presence of a solvent is also included.

TABLE I

Reaction Yields

| Example | Compound | Yield |
|---|---|---|
| 2 | 1 | <5% |
| 3 | 1 | 94% |
| 4 | 2 | 89% |
| 5 | 3 | 91% |
| 6 | 4 | 90% |
| 7 | 5 | 90% |
| 8 | 6 | 92% |
| 9 | 7 | 83% |
| 10 | 8 | 98% |
| 11 | 9 | 99% |
| 12 | 10 | 60% |

Example 14

Preparation of Antihypertensive Drugs using Compounds 1–10

Doxazosin

The synthesis of 4-amino-2-chloro-6,7-dimethoxyquinazoline can be found, for example, in GP 2857623 and J. Med. Chem. 30 (1987), 49.

4-amino-2-chloro-6,7-dimethoxyquinazoline (3.2 g, 13.35 mmol) and compound 1 (3.4 g, 13.75 mmol) prepared from Example 3 were dissolved in 72 mL of n-butanol. The mixture was refluxed under nitrogen for 3.5 hours. After cooling to 75° C., the solid product was obtained by filtration and dried to afford 5.25 g of hydrochloride salt of Doxazosin (10.76 mmol, 81% yield). 1 N NaOH solution was added to the salt. The mixture was heated to help the salt dissolved. After cooling, the mixture was extracted with 150 mL of dichloromethane twice. The organic layer was dried with anhydrous sodium sulfate and concentrated to afford 4.61 g of Doxazosin.

The product was white solid; 1H NMR(CDCl3) δ3.63–4.09 (m, 8H), 3.91 (s, 3H), 3.96 (s, 3H), 4.35 (dd, J=11.9, 7.9 Hz, 1H), 4.52 (dd, J=11.9, 2.4 Hz, 1H), 4.88 (dd, J=7.9, 2.4 Hz, 1H) , 6.85–6.95 (m, 5H)

Terazosin

The procedures were the same as described for Doxazosin, except that compound 3 (3.0 g, 16.3 mmol) prepared from Example 5 was reacted with 4-amino-2-chloro-6,7-dimethoxyquinazoline (3.8 g, 16.1 mmol) to provide 5.0 g of hydrochloride salt of Terazosin (73% yield), which is then converted to Terazosin (4.7 g, white solid) by alkalizing.

Other Quinazoline Derivatives

Procedures, similar to those described for Doxazosin, can be used to produce quinazoline derivatives, antihypertensive drugs. Intermediates amide compounds, as described above can be reacted with 4-amino-2-chloro-6,7-dimethoxyquinazoline to produce the hydrochloride salts of quanazoline derivatives.

For instance, compound 8 from Example 10 can be reacted with 4-amino-2-chloro-6,7-dimethoxyquinazoline to produce a quinazoline derivative of the formula:

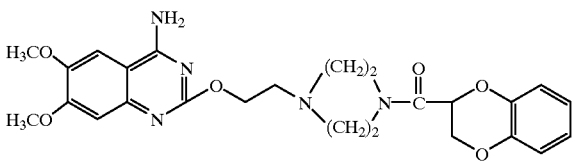

Alternatively, compound 9 from Example 11 can be reacted with reacted with 4-amino-2-chloro-6,7-dimethoxyquinazoline (III) to produce a quinazoline derivative of the formula:

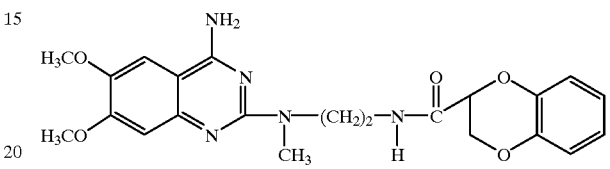

From the above examples, it can be seen that by using the method of the present invention to synthesis amide compounds, especially N-substituted carbonyl alkylenediamine compounds, the yield is very high. Neither solvents or catalysts are necessary for the reaction, therefore, the cost can be lowered to a great extent. There is no large amount of waste product will be generated except some methanol or ethanol, decreasing the risk of environmental pollution. Most importantly, according to the present invention, only one step is required for synthesizing N-substituted carbonyl alkylenediamine compounds. In contrast, conventionally, totally four steps are required for synthesizing N-substituted carbonyl alkylenediamine compounds. Thus, according to the present invention, the reaction procedures are extensively decreased, and the yield is extensively increased 40–50% , which are advantageous over the conventional method.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for preparing a tertiary amide, said process comprising contacting, in the absence of a solvent, a secondary amine with an ester, wherein the secondary amine is an alkylenediamine, and both the secondary amine and the ester are in a molten form at a temperature of 60° C. to 130° C.

2. The process of claim 1, for preparing a N-substituted carbonyl alkylenediamine, wherein the secondary amine is

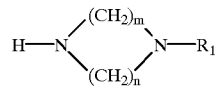

in which $R_1$ is selected from the group consisting of H, C1–8 alkyl, C1–8 alkenyl, C1–8 heteroalkyl, and C1–8 heteroalkenyl; m is 2 or 3; and n is 2 or 3; or

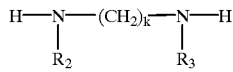

in which each of $R_2$ and $R_3$ is independently selected from the group consisting of H, C1–8 alkyl, C1–8 alkenyl, C1–8 heteroalkyl, and C1–8 heteroalkenyl; k is 1 to 8; and the ester is

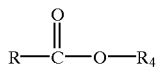

in which R is selected from the group consisting of C1–8 alkyl, C1–8 alkenyl, C3–8 cycloalkyl, C3–8 cycloalkenyl, C4–8 aryl, C2–8 heterocycle; and $R_4$ is C1–8 alkyl or C1–8 alkenyl.

3. The process of claim 2, wherein R1 is selected from the group consisting of H, unsubstituted C1–8 alkyl, hydroxy substituted C1–8 alkyl, sulfhydryl substituted C1–8 alkyl, and amino substituted C1–8 alkyl.

4. The process of claim 2, wherein each of R2 and R3 is independently selected from the group consisting of H, unsubstituted C1–8 alkyl, hydroxy substituted C1–8 alkyl, sulfhydryl substituted C1–8 alkyl, and amino substituted C1–8 alkyl.

5. The process of claim 2, wherein the substituent of R in the ester is selected from the group consisting of C2–8 heterocycle, unsubstituted C1–8 alkyl, hydroxy substituted C1–8 alkyl, and alkoxy substituted C1–8 alkyl.

6. The process of claim 5, wherein R in the ester is selected from the group consisting of

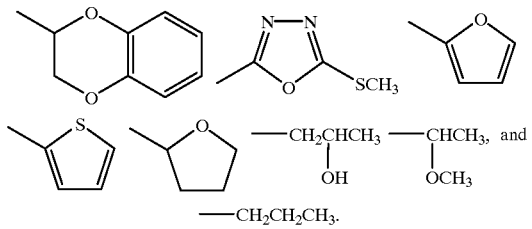

7. A process of claim 1 for preparing a quinazoline derivative, the process comprising contacting, in the absence of a solvent, an secondary amine in a molten form with an ester in a molten form to form an N-substituted carbonyl alkylenediamine, wherein the secondary amine is $$H-N\overset{(CH_2)_m}{\underset{(CH_2)_n}{\diagup\hspace{-0.5em}\diagdown}}N-R_1$$

in which $R_1$ is selected from the group consisting of H, C1–8 alkyl, C1–8 alkenyl, C1–8 heteroalkyl, and C1–8 heteroalkenyl; m is 2 or 3; and n is 2 or 3; or $$H-N(R_2)-(CH_2)_k-N(R_3)-H$$

in which each of R2 and R3 is independently selected from the group consisting of H, C1–8 alkyl, C1–8 alkenyl, C1–8 heteroalkyl, and C1–8 heteroalkenyl; k is 1 to 8; and the ester is $$R-C(=O)-O-R_4$$

in which R is selected from the group consisting of C1–8 alkyl, C1–8 alkenyl, C3–8 cycloalkyl, C3–8 cycloalkenyl, C4–8 aryl, C2–8 heterocycle; and R4 is C1–8 alkyl or C1–8 alkenyl; and contacting said N-substituted carbonyl alkylenediamine with a quinazoline to form a quinazoline derivative, wherein said quinazoline derivative is

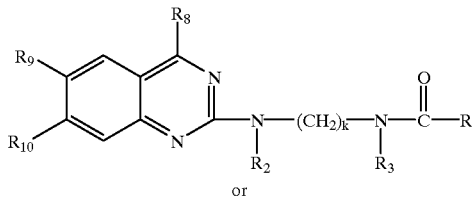

or in which R, m, and n are defined above; and each of R8–R10 is independently selected from the group consisting of halogen, hydrogen, amino, C1–8 alkyl, C1–8 alkenyl, C3–8 cycloalkyl, C3–8 cycloalkenyl, C4–8 aryl, C1–8 alkoxyl, C1–8 alkylthio, C3–8 heterocycle; X is selected from N, O, or S; and R5 is selected from the group consisting of C1–8 alkyl, C1–8 alkenyl, C1–8 heteroalkyl, and C1–8 heteroalkenyl; or

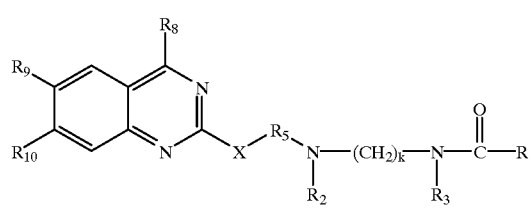

in which R, R2, R3, R8–R10, X, R5, and k are defined above.

8. The process of claim 7, wherein R1 is selected from the group consisting of H, unsubstituted C1–8 alkyl, hydroxy substituted C1–8 alkyl, sulfhydryl substituted C1–8 alkyl, and amino substituted C1–8 alkyl.

9. The process of claim 7, wherein R5 is selected from the group consisting of C1–8 alkyl, hydroxy substituted C1–8 alkyl, sulfhydryl substituted C1–8 alkyl, and amino substituted C1–8 alkyl.

10. The process of claim 7, wherein each of R2 and R3 is independently selected from the group consisting of H, unsubstituted C1–8 alkyl, hydroxy substituted C1–8 alkyl, sulfhydryl substituted C1–8 alkyl, and amino substituted C1–8 alkyl.

11. The process of claim 7, wherein the substituent of R in the ester is selected from the group consisting of C2–8 heterocycle, unsubstituted C1–8 alkyl, hydroxy substituted C1–8 alkyl, and alkoxy substituted C1–8 alkyl.

12. The process of claim 11, wherein R in the ester is selected from the group consisting of

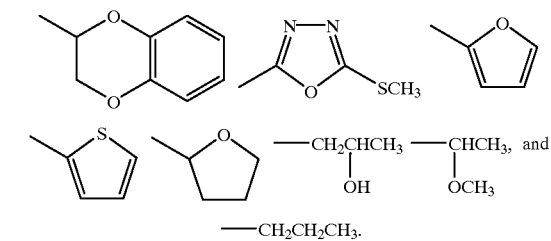

13. The process of claim 1, wherein the secondary amine and the ester are in a molten form at a temperature of about 100° to 120° C.

14. The process of claim 1, wherein the secondary amine and the ester are reacted in a molten form in the absence of a catalyst.

* * * * *